(12) United States Patent
Shulman

(10) Patent No.: US 7,253,899 B2
(45) Date of Patent: Aug. 7, 2007

(54) APPARATUS AND METHOD FOR MEASURING OPTICALLY ACTIVE MATERIALS

(75) Inventor: Yaacov Shulman, Jerusalem (IL)

(73) Assignee: Vinoron Technologies Limited, Har Hotzvim, Jerusalem (IL)

( * ) Notice: Subject to any disclaimer, the term of this patent is extended or adjusted under 35 U.S.C. 154(b) by 293 days.

(21) Appl. No.: 10/489,870

(22) PCT Filed: Sep. 18, 2002

(86) PCT No.: PCT/IL02/00774

§ 371 (c)(1), (2), (4) Date: Jul. 8, 2004

(87) PCT Pub. No.: WO03/027645

PCT Pub. Date: Apr. 3, 2003

(65) Prior Publication Data

US 2004/0238361 A1  Dec. 2, 2004

(30) Foreign Application Priority Data

Sep. 26, 2001 (IL) .................................. 145683

(51) Int. Cl.
*G01J 4/00* (2006.01)
(52) U.S. Cl. ................ 356/364; 356/367; 356/368
(58) Field of Classification Search ........ 356/364–368; 250/343; 359/485; 600/316–326
See application file for complete search history.

(56) References Cited

U.S. PATENT DOCUMENTS

| | | | |
|---|---|---|---|
| 2,829,555 A * | 4/1958 | Keston ..................... 356/368 |
| 3,510,222 A | 5/1970 | Shaw, Jr. | |
| 4,427,889 A | 1/1984 | Muller | |
| 4,467,204 A * | 8/1984 | Kysilka et al. ............. 250/343 |
| 4,988,199 A * | 1/1991 | Paul ........................ 356/368 |
| 5,012,101 A * | 4/1991 | Goodall et al. ............ 250/343 |
| 5,372,136 A * | 12/1994 | Steuer et al. .............. 600/326 |
| 5,687,721 A * | 11/1997 | Kuhls ....................... 600/316 |
| 6,466,320 B1 * | 10/2002 | Kawamura et al. ........ 356/364 |
| 6,794,195 B2 * | 9/2004 | Colvin, Jr. ................. 436/95 |

FOREIGN PATENT DOCUMENTS

| | | |
|---|---|---|
| DE | 2724543 | 12/1978 |
| GB | 1167519 | 10/1969 |
| GB | 2181231 | 4/1987 |

* cited by examiner

*Primary Examiner*—Gregory J. Toatley, Jr.
*Assistant Examiner*—Jarreas C. Underwood
(74) *Attorney, Agent, or Firm*—Dennison, Schultz & MacDonald

(57) ABSTRACT

Apparatus and method for sensing and measuring optically active material in a sample, comprising:
  a) a light source emitting light of a wavelength that can pass through the sample;
  b) a light transparent sample container for holding the sample;
  c) a linear polarizer interposed between the light source and the sample for producing a polarized light beam;
  d) a symmetrical linear split-field polarizer fixedly positioned to intercept the polarized light that passed through the sample;
  e) detectors to detect the split light beams passing through each polarizer of the split-field polarizer;
  f) means to amplify the current or voltage passing through each of the detectors;
  g) a differential amplifier;
  h) a data processor;
  i) a display; and
  j) electronic circuitry to operate the apparatus and provide an output on the display.

23 Claims, 4 Drawing Sheets

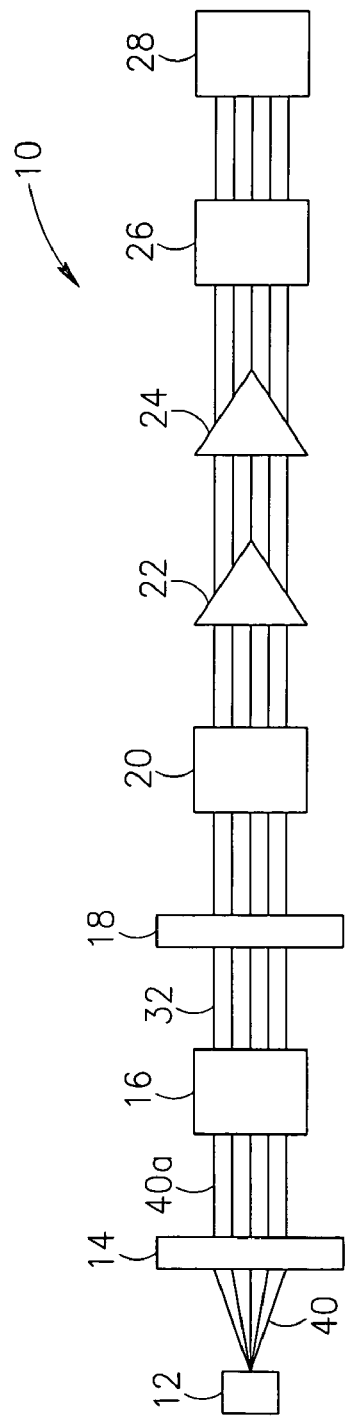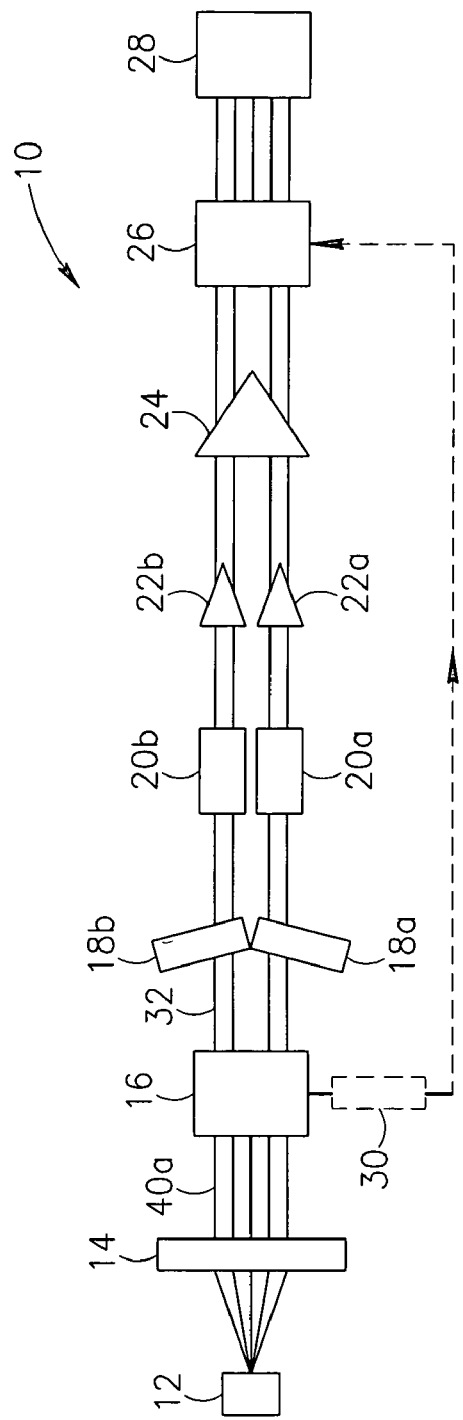
FIG.1A
FIG.1B

APPARATUS AND METHOD FOR MEASURING OPTICALLY ACTIVE MATERIALS

This application is a filing under 35 USC 371 of PCT/IL02/00774, filed Sep. 18, 2002.

FIELD OF THE INVENTION

This invention relates generally to an apparatus and method for measuring optically active materials, particularly in liquid solutions. More specifically, this invention relates to an apparatus and method for measuring sugars in natural beverages such as wine, beer, grape juice etc.

BACKGROUND OF THE INVENTION

Certain solutions, e.g. containing sugar, possess the property of being able to rotate the plane of linear polarized light. The degree of rotation of the plane of vibration per unit of the solution traversed by the polarized light varies in accordance with the concentration of the solution. It is well known in the art to use a device having a light polarizer and an analyzer to measure the rotation of the plane of vibration of light passing through a solution, and to thereby determine the percent sugar content of the solution. One example of such an apparatus is shown in U.S. Pat. No. 3,411,342. In this patent, the polarimeter consists of a mercury vapor lamp light source, a collimating lens, a primary polarizer to establish a reference point for measurement of optical rotation, a sample cell through which a continuous stream of crude syrup is circulated, and a measuring circuit that determines the extent of optical rotation caused by the sample and provides an appropriate output signal.

Such conventional polarimeters of the prior art generally use visible light sources in the 400-700 nanometer wavelength emission range.

U.S. Pat. No. 4,467,204 describes a polarimeter system and method using an infrared light source to gauge and measure the optical rotation of dark sugar solutions.

German Patent No. 2724543 and U.S. Pat. Nos. 3,724,957; 4,699,514 and 4,671,660 disclose multi-beam measurement of polarimetry.

U.S. Pat. No. 5,009,230 describes a device for polarimetrically measuring the concentration of blood glucose by producing two alternating linearly polarized states of infrared light, passing these through a sample, detecting the intensities of these two states after passing through the sample and detector and calculation means for measuring the ratio of the sum and differences of the transmitted intensities.

U.S. Pat. Nos. 4,167,676; 4,350,163; 4,427,889; 4,586,513 and 4,655,225 describe polarimetric devices using absorption and/or backscattering of incident radiation to determine glucose levels.

None of these known devices have the sensitivity achievable by more rigorous available analytical techniques. The degree of rotation caused by glucose levels of the body, for example, is very small and is normally difficult to measure with any sensitivity without using large and bulky equipment and invasive procedures.

SUMMARY OF THE INVENTION

It is an object of this invention to provide an apparatus and method for quantitatively measuring the concentration of optically active materials in solution.

Another object of the invention is to provide an apparatus and method for quantitatively measuring one or more optically active materials in a solution.

Yet another object of the invention is to provide a compact portable polarimeter that is simple to operate.

A further specific objective of the invention is to provide an apparatus and method for quantitatively measuring the concentration of glucose and/or fructose in natural beverages.

Still another object of the invention is to measure the concentration of sugars in natural beverages containing alcohol.

In accordance with this invention there is thus provided an apparatus for sensing and measuring the concentration of optically active material in a liquid sample, comprising:

a) a light source emitting light of a wavelength that can pass through the sample;

b) a light transparent sample container for holding the sample;

c) a linear polarizer interposed between the light source and the sample for producing a polarized light beam;

d) a symmetrical linear split-field polarizer fixedly positioned to intercept the polarized light that passed through the sample;

e) detectors to detect the split light beams passing through each polarizer of the split-field polarizer and convert the light to current or voltage;

f) means to amplify the current or voltage passing through each of the detectors;

g) a differential amplifier;

h) a data processor;

i) a display; and j) electronic circuitry to operate the apparatus and provide an output on the display.

The light source may be one that is selectable to emit light of different wavelengths.

The apparatus may also have collimating optics to focus the light from the source on the sample. The sample container or cell may be modified for on-line continuous process testing.

The light source can be any known light source used in polarimetry, UV, IR or visible, in the range of 300 to 1100 nanometers, but for practical reasons and simplicity it is preferred to use LEDs. For determining sugars in natural beverages, light in the visible and IR range between 400-800 nanometers, is used. When determining the concentration of optically active material, each having a different optical rotation at different wavelengths, it is possible to use light sources of different wavelengths to measure one component, then the other. LEDs containing more than one light source, each of a different wavelength are now available commercially and are useful in spite of the fact that they have a bandpass around the peak wavelength.

The sample container should have maximum light transparency without distorting optical activity. Such containers or cells are well known from conventional polarimeters and optical measuring devices.

The linear polarizer and symmetrical linear split-field polarizer can be made of calcite crystals and preferably from plastic sheet material as is known in the art. The split-field polarizer in accordance with this invention should have a separation angle of 45° or less from the median line between them, which can be expressed as $\frac{1}{2}\delta=45°$, preferably $\frac{1}{2}\delta=20\text{-}30°$, where $\delta$ is the angle between the split-field polarizers. The polarity of these polarizers is about $90°\pm\frac{1}{2}\delta$ with respect of the first linear polarizer.

The detectors or sensors are preferably photodiodes which convert the intensity of the light passing through the polarizers into electrical impulses. These impulses may be amplified, then passed through a differential amplifier which feeds the difference in light intensity between the two halves of the split-field polarizer to a data processor that computes the results in percent concentration by comparing the intensities with known standard intensity data charts for the particular solution of optically active material. It is also possible to include temperature measuring and/or control facilities in the sample container and provide this information to the processor.

The present invention also includes the possibility of measuring only one detector, and divide the result by the measurement difference of the two detectors. The process of dividing, storing in the memory, and switching off the second detector is accomplished by a processor. Moreover, it is also possible to use an IR light source whose wavelength has little or no effect on the optically active material nor on the linear polarizers, to get an independent reference measurement. This reference measurement can be compared with measurements taken at the wavelengths of visible light or IR, which are influenced by the optically active material and the linear polarizer, to classify the color or opacity (darkness) of the solution for each measurement.

The present invention has the advantage in that light which passes through the two polarizers and exits as noise, and not as a result of optical activity, vanishes because of the action of the differential amplifier.

BRIEF DESCRIPTION OF THE DRAWINGS

The invention will be better understood in conjunction with the drawings in which:

FIGS. 1A and 1B are schematic plan and top view diagrams illustrating a polarimeter constructed in accordance with the invention;

DETAILED DESCRIPTION OF THE INVENTION

Figure 4:
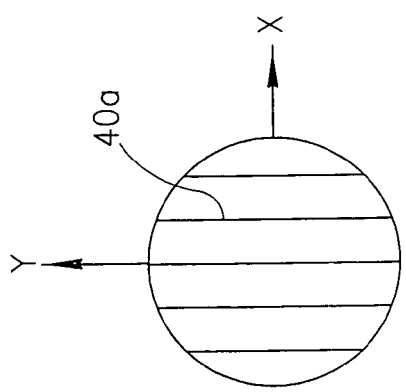
FIG. 4 shows a cross-section of a linear polarized ray of light in the y direction.

Referring now to FIGS. 1A and 1B, these show a plan and top view, respectively, of apparatus 10, according to the invention. Apparatus 10 consists of a light source 12, a linear polarizer 14, a sample container (cell) 16, symmetrical linear split-field polarizer 18, detectors 20, amplifiers 22, differential amplifier 24, processor 26 and display 28. There may also be a thermometer 30 connected to the sample container 16 to monitor the sample temperatures and feed this information electronically to the processor 26 for incorporation into the final calculation. The display 28 shows the results in percent concentration and/or any other form as pre-programmed.

The heart of the invention resides in the combination of a symmetrical linear split-field polarizer 18 with conventional polarimeter technology. This combination makes it easier and is more sensitive to measuring optically active materials in solutions. Although linear split-field polarizers were known in polarimetry to obtain more accurate measurements, this was accomplished by rotating the polarizers. The split-field polarizers were never used in a fixed position.

We shall now try to explain the principle behind this invention.

Figure 2:
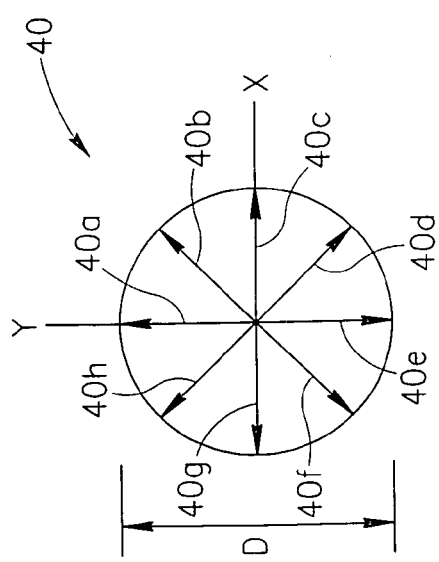
FIG. 2 illustrates a cross-section of a ray of light.

Referring to FIG. 2, we can visualize a ray of light 40 having a diameter D moving along the z axis, i.e., in the plane inside this page. This ray of light 40 has wave amplitudes 40a-40h which are at random angles to the y axis. It is customary to visualize a ray of light as having two components of polarization, one in the x-axis and the other in the y-axis, FIG. 3.

Figure 3:
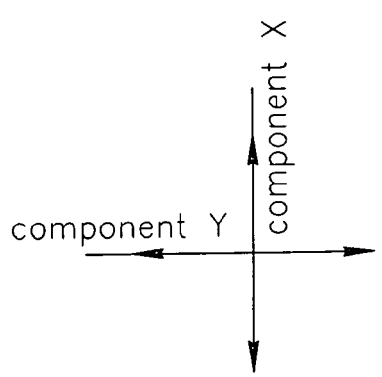
FIG. 3 "visualizes" the ray of light of FIG. 1 along the x and y axis.
Figure 5:
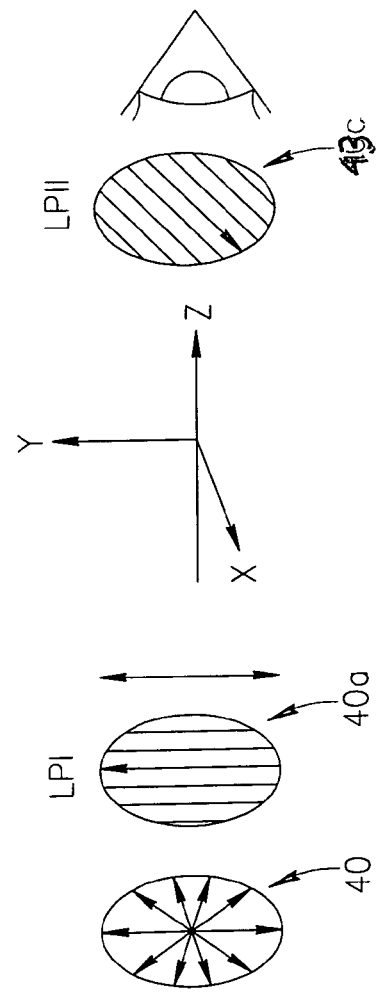
FIG. 5 illustrates light transmission through two linear polarizers LPI and LPII at 90° of each other.

When such a ray of light 40 is directed through a linear polarizer, the light rays passing through will be only those having the same directional component as the polarizer, for example, in the y direction (FIG. 3). Light having the other directional component x is not transmitted. When this polarized light passes through a second Linear Polarizer II, in the x direction (perpendicular to Linear Polarizer I), the ray is no longer visible, FIG. 5.

The Polarimeter

Figure 6:
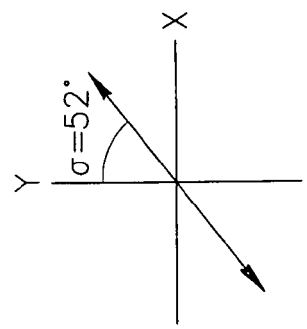
FIG. 6 illustrates the rotation of polarized light passing through an optically active material.

A polarized ray of light in the y direction that passes through a material having optical activity will undergo a change in its angle of rotation. The change in angle of rotation $\sigma$, in relation to the y-axis is called the Optical Rotation Dispersion (ORD). For example, a polarized ray of light 40a that passes through a 10 cm long solution of glucose in water having a concentration of 100 g/dL, results in a rotation of the ray by 52° in relation to the y-axis, FIG. 6. This occurs under the conditions that the wavelength of the light is $\lambda=5460A°$ at a temperature of 20° C. A change in the wavelength $\lambda$ will cause a change in $\sigma$, even when the concentration is not changed. This is known as the Dispersion Factor.

Figure 7:
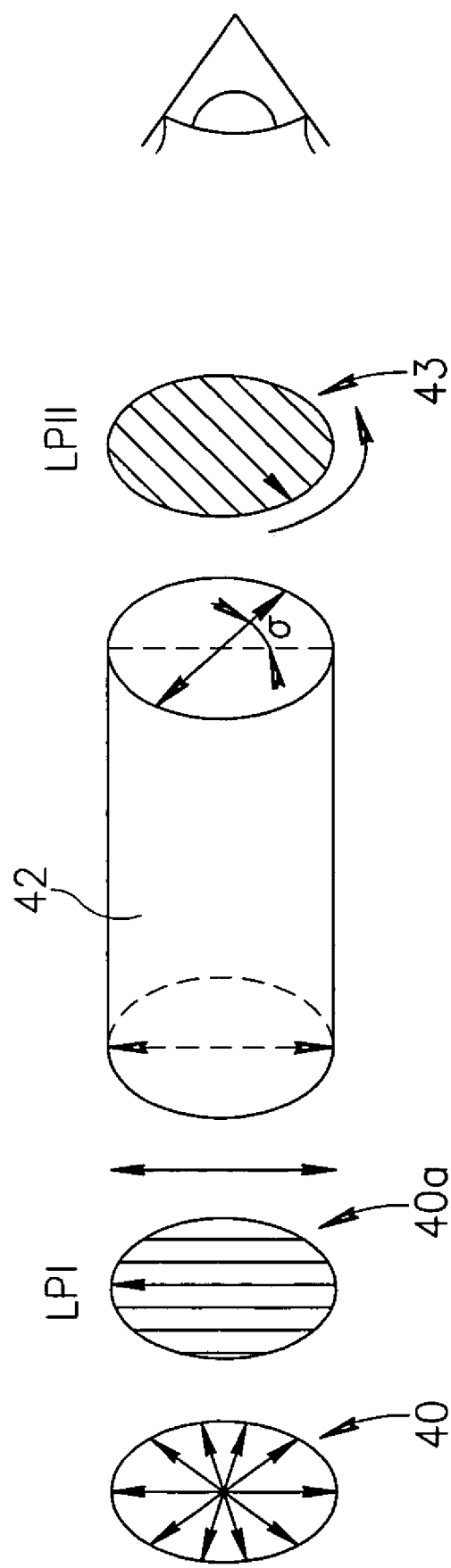
FIG. 7 illustrates the actual light transmission through an optically active material with linear polarizers before and after the sample.

Referring now to FIG. 7, in a polarimeter, when a solution 42 of optically active material, such as an aqueous glucose solution, is placed between the two Linear Polarizers LPI and LPII set at 90° of each other (FIG. 7), the polarized light component y that exits LPI and passes through the solution 42 will now rotate to an angle of $\sigma$ in relation to the y-axis. When this rotated light at angle $\sigma$ passes through the second polarizer LPII it does not vanish, because the angle between this light 43 and LPII is not 90°. Therefore the light 43 will be visible to the eye.

In the traditional polarimeter the rotational angle, $\sigma$, is measured by rotating LPII until the light is not visible to the eye. This angle of rotation is equal to the rotation of the light by the glucose solution.

In modern polarimeters the eye is replaced with a photoelectric detector that is connected to a microcomputer. The polarizers are controlled much more accurately. The light source may be modulated or non-modulated.

The accuracy in the traditional polarimeter is 0.02°. The accuracy in the modern polarimeter is 0.003°.

Split Field Polarization

A symmetrical linear split-field polarizer consists of two linear polarizers LPIIA and LPIIB set at an angle $\delta$ between the two. Each polarizer polarizes light in the same amount, for example, in the y axis. One polarizer is set at an angle of $+\frac{1}{2}\delta$ and the other polarizer is at an angle of $-\frac{1}{2}\delta$ in relation to the y-axis (see FIG. 8).

Principle of the Invention

Figure 8:
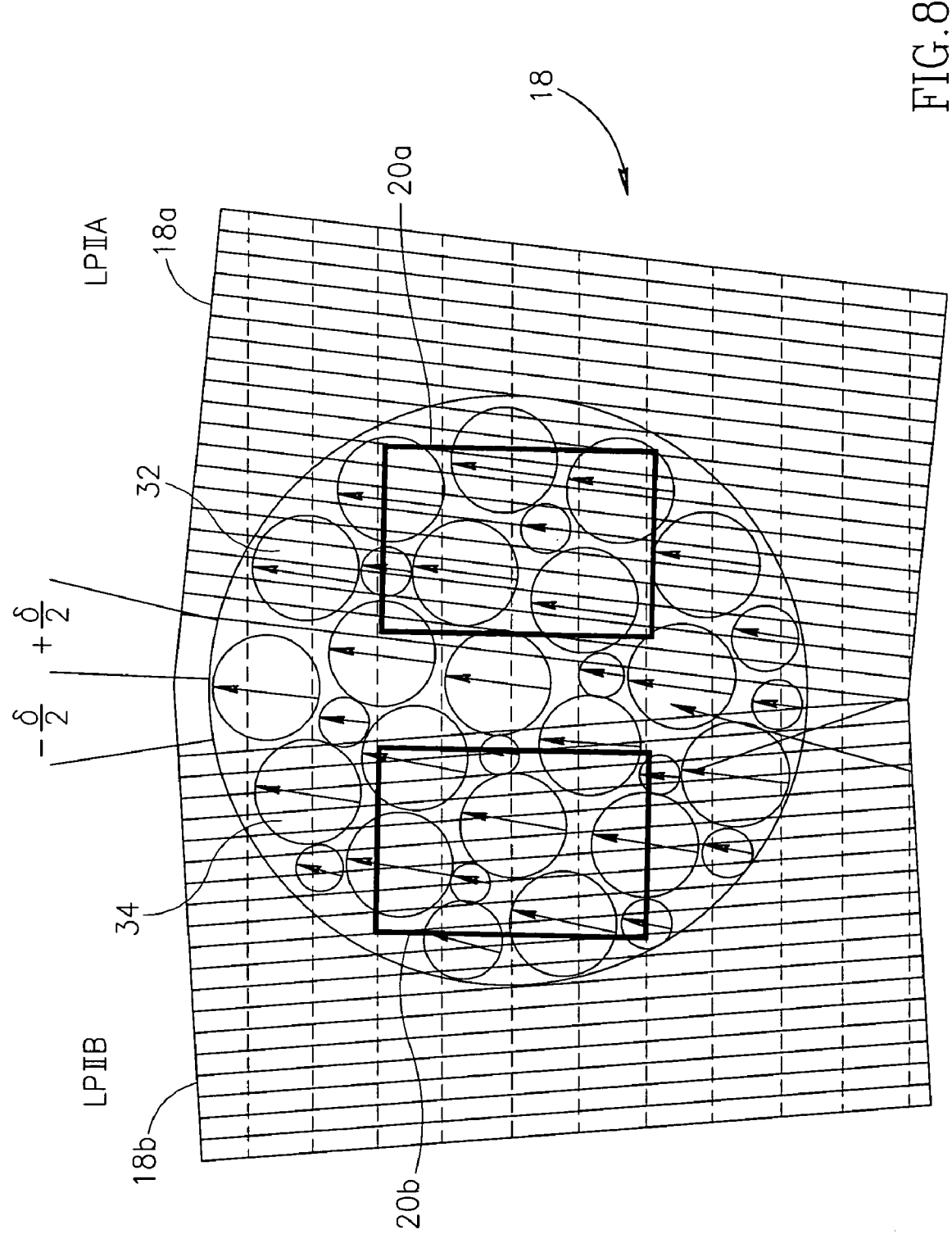
FIG. 8 illustrates photodetection of symmetrical linear split-field polarized light according to the invention.

The invention will be described with reference to FIGS. 1A, 1B and 8. Polarized light 40a is passed through a sample 16 containing optically active material, such as glucose. A symmetrical split-field polarizer 18 (18a, 18b) is placed in front of photoelectric detectors 20 (20a, 20b). The split-field polarizer 18 having an angle δ between the polarizers 18a and 18b. Assume that the polarized light 32 after it passes through the sample 16 is rotated to a maximum angle σ=+½δ in relation to the y-axis. In relation to LPIIA 18a, the polarized light 32 is transmitted in parallel. However, relative to LPIIB 18b, the polarized light 34 is at an angle of δ.

According to Malus Law, polarized light at an intensity of $I_{in}$ that passes through a Linear Polarizer exits at an intensity of $I_{out}$. The relationship between $I_{in}$ and $I_{out}$ can be expressed as follows:

$$I_{out} = I_{in} \cos^2 \varnothing$$

where ⌀ is the angle between the Linear Polarizer and the entering polarized light. The rotated polarized light that passes through LPIIA has no change in the intensity because the light is in parallel relative to LPIIA. Therefore, ⌀=0°, $\cos^2 \varnothing = 1$ and $I^{IIA}_{out} = I^{IIA}_{in}$. The polarized light that passes through LPIIB has a decreased Intensity because the polarized light is at an angle of δ relative to LPIIB. Thus, when ⌀=δ the Intensity equation is $I^{IIB}_{out} = I^{IIB}_{in} \cos^2 \delta$.

We assume that the intensity of the polarized light entering each Polarizer is equal, i.e., $I^{IIA}_{in} = I^{IIB}_{in}$. Since $I^{IIA}_{out} = I^{IIA}_{in}$ and $I^{IIB}_{out} = I^{IIB}_{in} \cos^2 \delta$, therefore $I^{IIB}_{out} = I^{IIA}_{out} \cos^2 \delta$. The relationship between the two light intensities passing through the two parts of the split field-polarizer with a maximum rotation angle ½ δ is $$\frac{I^{IIB}_{out}}{I^{IIA}_{out}} = \cos^2 \delta.$$

According to the Responsivity of the detectors the photocurrent, i, is equal to 0.3 amp per watt absorbed by the detector for λ=5000 A°. Therefore:

$i^{IIA} = I^{IIA}_{out} 0.3$ and $i^{IIA} = I^{IIA}_{out} 0.3$. Then:

$i^{IIA}/i^{IIB} = I^{IIA}_{out}/I^{IIB}_{out}$ and $I^{IIA}_{out} = I^{IIB}_{out} \cos^2 \delta$ $i^{IIA}/i^{IIB} = \cos^2 \delta$ The relationship of the photocurrents in the detectors 20A and 20B with a maximum rotation ½ δ is $$\frac{i^{IIB}}{i^{IIA}} = \cos^2 \delta$$

Thus the present invention provides a powerful instrument to measure the rotation of polarized light that passes through the glucose-water solution as a function of the concentration. As the concentration of the glucose increases, the rotation angle σ increases and the difference in the current between the two detectors 20a and 20b also increases.

The sensitivity of the detectors is about 1 picoamp ($10^{-12}$ amperes). The minimum power requirement to generate this photocurrent is 1 picowatt. Thus the minimum power difference between the two rays of light that are absorbed by the two detectors must be at least 1 picowatt. $\sigma_{min}$ is the minimum angle of rotation relative to the y axis that provides an adequate difference in the power of the lights. This difference can be expressed mathematically as:

$$I^{IIA}_{in} \cos^2(\tfrac{1}{2}\delta - \alpha) - I^{IIB}_{in} \cos^2(\tfrac{1}{2}\delta + \alpha)$$

When there is no rotation, α=0 and since $I^{IIA}_{in} = I^{IIB}_{in} = I_{in}$ the above equation is equal to zero. For $\alpha_{min}$:

$$I_{in}(\cos^2(\tfrac{1}{2}\delta - \alpha) - \cos^2(\tfrac{1}{2}\delta + \alpha)) = 10^{-12}$$

This can be converted trigonometrically to:

$I_{in} \sin \delta \sin 2\alpha = 10^{-12}$ $\sin 2\alpha = 10^{-12}/I_{in} \sin \delta$ For $I_{in} = 10^{-6}$ watt and δ=1° then $\alpha_{min} = 1.64 \cdot 10^{-3}$ For $I_{in} = 10^{-4}$ watt and δ=1° then $\alpha_{min} = 1.64 \cdot 10^{-5}$ Thus for $I_{in} = 10^{-6}$ watt the minimum degree of rotation, $\alpha_{min}$ is measured in mili degrees. For $I_{in} = 10^{-4}$ watt the minimum degree of rotation, $\alpha_{min}$, is measured in tens of micro degrees.

Therefore, the accuracy of this invention is 100 times greater than the reported accuracy in U.S. Pat. No. 5,009,230.

For $I_{in} = 10^{-6}$ watt and δ=25° then $\alpha_{min} = 6.7 \cdot 10^{-5}$

For $I_{in} = 10^{-4}$ watt and δ=25° then $\alpha_{min} = 6.7 \cdot 10^{-7}$

Thus for $I_{in} = 10^{-6}$ watt the minimum degree of rotation, $\alpha_{min}$ is measured in tens of micro degrees. For $I_{in} = 10^{-4}$ watt the minimum degree of rotation, $\alpha_{min}$, is measured in hundreds of nano degrees.

Therefore, the accuracy of this invention is 10000 times greater than the reported accuracy in U.S. Pat. No. 5,009,230.

Since this invention is based on the difference in the reading of the two detectors, any signal not generated by the polarization of light is common in both detectors and is cancelled out by the differential amplifier.

The detectors 20a and 20b can be calibrated so as to compensate for any unequal detection by passing light through an empty cell, which should show no rotation on the display 28. If some rotation does show, the intensity of the light of one of the detectors can be adjusted electronically or opto-mechanically to show no rotation. One of the ways to make such an opto-mechanical adjustment of a detector is to block some of the light entering the detector. To check the linearity of the system, it should be tested with a known standard concentration.

The present invention does not require a reference beam.

A particular advantage of the present invention is that one can determine the concentrations of both glucose and fructose in one solution. Glucose and fructose have different Optical Rotational Dispersions (ORD) in opposite directions. Thus it is possible to measure the concentration of each component in a mixture by measuring the OR of each component sequentially at their respective optimal wavelengths and calculating the concentrations by comparison with a data base of known concentrations of mixtures.

To illustrate the invention let us take for example the following: Solutions of 100 grams glucose or fructose in 100 ml of water at 20° C. have the following Specific Rotations:

|  | Glucose | Fructose |
| --- | --- | --- |
| at λ = 5460 Å | +52° | −106° |
| at λ = 5080 Å | +73° | −136° |

Therefore, a mixture of 100 grams glucose and 100 grams fructose in 100 ml water should have the following Rotation:

a) at λ=5460 Å +52°+(−106°)=−54°
b) at λ=5080 Å +73°+(−136°)=−63°

According to reading a) this represents the equivalent of 51 g/100 ml fructose, and according to reading b) it represents the equivalent of 46.3 g/100 ml fructose. From these two measurements we learn first, that there is an optically active component in the solution in addition to fructose, and second, the exact concentration of each component in the mixture can be determined by comparing the results of the readings [a) and b)] with a data base of the Rotations of known mixtures of glucose and fructose.

An apparatus as described above was constructed having the following components:
1) light source: LED-HLMP 3850, wavelength λ=5830 Å, manufactured by HP;
2) linear polarizer: type HN 32, manufactured by Polaroid. The angle between LPIIA and LPIIB was =5°;
3) sample container: 10 mm×10 mm×30 mm glass;
4) photodetectors (2): LDR-type P1241-12(E), (CdS photo-conductive cells where the resistance decreases when the light increases);
5) differential amplifier: LM 741 CN-8, manufactured by National Semiconductor;
6) display: DMM—(Digital Multi Meter) having a resolution of 3½ digits.

EXAMPLE

The optical rotation of pure water and different concentrations of glucose in water were determined at 25° C. and atmospheric pressure as shown in the Table. The positive reading for pure water was expected because of variations in the manufacturing process of the two detectors. This reading can be adjusted to zero and all other readings calibrated accordingly. By plotting the glucose concentration vs. optical rotation of known samples (using a wider range of concentrations) one can prepare a reference chart, and unknown concentrations of glucose can be quantitatively determined by comparison with the chart.

TABLE

| Sample/100 ml water | OR[1] mV | OR[1] mV-after adjustment |
|---|---|---|
| Pure water | +247 | 0 |
| 5 g glucose | +44 | −203 |
| 10 g glucose | −208 | −455 |
| 15 g glucose | −283 | −530 |
| 19 g glucose | −300 | −547 |

[1]Optical Rotation

The apparatus of the present invention can be used not only to detect sugars in blood, urine, fruit juices and other solutions but also to detect and determine other optically active materials in solutions, for example drugs.

It will be appreciated by persons skilled in the art that the scope of the present invention is not limited to what has been shown and described hereinabove, merely by way of example. Rather, the scope of the invention is limited solely by the claims which follow.

The invention claimed is:

1. Apparatus for sensing and measuring optically active material in a sample, comprising:
   a) a light source emitting light of a wavelength that can pass through the sample;
   b) a light transparent sample container for holding the sample;
   c) a linear polarizer interposed between the light source and the sample for producing a polarized light beam;
   d) a symmetrical linear split-field polarizer having a separation angle expressed as ½δ=12.5°-30°, and a polarity from about 90°±45° to 90°±½° with respect to the first linear polarizer, said polarizer being fixedly positioned to intercept the polarized light that passed through the sample;
   e) detectors to detect the split light beams passing through each polarizer of the split-field polarizer;
   f) means to amplify the current or voltage passing through each of the detectors;
   g) a differential amplifier;
   h) a data processor;
   i) a display; and
   j) electronic circuitry to operate the apparatus and provide an output on the display.

2. Apparatus as in claim 1, further comprising colimating optics to focus the light from the light source.

3. Apparatus as in claim 1, wherein the light source is a LED.

4. Apparatus as in claim 1, wherein the light source is a selectable light source able to select light of different wavelengths.

5. Apparatus as in claim 1, wherein the emitted light is selected from UV, IR and visible range.

6. Apparatus as in claim 1, wherein the light has a wavelength between 300-1100 nanometers.

7. Apparatus as in claim 1, wherein the light has a wavelength between 400-800 nanometers.

8. Apparatus as in claim 1, wherein a single light source can provide selectively light at different wavelengths.

9. Apparatus as in claim 1, wherein the detectors have adjusting means.

10. Apparatus as in claim 1, for measuring the concentration of sugars in solutions.

11. Apparatus as in claim 9, for measuring glucose and/or fructose in natural beverages.

12. A method of measuring and/or identifying optically active materials in solutions polarimetrically, comprising:
   a) providing a sample containing an optically active material;
   b) placing the sample in the sample container of the apparatus of claim 1;
   c) providing a light source of suitable wavelength for determining the particular optically active material;
   d) activate the light source to pass polarized light through the sample and through the split-field polarizer;
   e) amplifying and measuring the intensity difference of the light passing through the symmetrical linear split-field polarizer and calculating the concentration of the optically active material; and
   f) display the results.

13. A method as in claim 12, wherein the optically active material is a solution containing glucose, fructose or a mixture thereof.

14. A method as in claim 12, wherein the sample contains more than one optically active material and the light source emits selectively light of different wavelengths, and the measurement and calculation is conducted for each optically active component at a different wavelength.

15. A method as in claim 13, wherein the sample is a fruit juice.

16. A method as in claim 13, wherein the sample is wine fermentation.

17. A method as in claim 12, wherein the sample is a blood sample.

18. A method as in claim 12, wherein the sample is urine.

19. A method as in claim 12, wherein the optically active material is a drug.

20. An apparatus as claimed in claim 1 that is compact and hand portable.

21. An apparatus as in claim 1 wherein the means to amplify comprise resistors and high voltage.

22. Apparatus as in claim 1, wherein the symmetrical linear split-field polarizer has a separation angle expressed as ½δ=20°-30°.

23. Apparatus for sensing and measuring optically active material in a sample, comprising:
- a) a light source emitting light of a wavelength that can pass through the sample;
- b) a light transparent sample container 30 mm in length for holding the sample;
- c) a linear polarizer interposed between the light source and the sample for producing a polarized light beam;
- d) a symmetrical linear split-field polarizer having a polarity from about 90°±45° to 90°±½° with respect to the first linear polarizer, said polarizer being fixedly positioned to intercept the polarized light that passed through the sample;
- e) detectors to detect the split light beams passing through each polarizer of the split-field polarizer;
- f) means to amplify the current or voltage passing through each of the detectors;
- g) a differential amplifier;
- h) a data processor;
- i) a display; and
- j) electronic circuitry to operate the apparatus and provide an output on the display.

\* \* \* \* \*